(12) United States Patent
Zhu et al.

(10) Patent No.: US 11,187,691 B2
(45) Date of Patent: Nov. 30, 2021

(54) PRESSURE-CONTROL TEMPERATURE-CONTROL HYPERGRAVITY EXPERIMENTAL DEVICE FOR SIMULATING DEEP-SEA SEABED RESPONSES

(71) Applicant: ZHEJIANG UNIVERSITY, Zhejiang (CN)

(72) Inventors: Bin Zhu, Zhejiang (CN); Lujun Wang, Zhejiang (CN); Songqing Yang, Zhejiang (CN); Yunmin Chen, Zhejiang (CN); Deqiong Kong, Zhejiang (CN); Weian Lin, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 0 days.

(21) Appl. No.: 17/253,122

(22) PCT Filed: Mar. 4, 2019

(86) PCT No.: PCT/CN2019/076791
§ 371 (c)(1),
(2) Date: Dec. 17, 2020

(87) PCT Pub. No.: WO2019/170044
PCT Pub. Date: Sep. 12, 2019

(65) Prior Publication Data
US 2021/0263005 A1 Aug. 26, 2021

(30) Foreign Application Priority Data

Mar. 5, 2018 (CN) .......................... 201810178557.2
Mar. 5, 2018 (CN) .......................... 201810178558.7

(51) Int. Cl.
*G01N 33/24* (2006.01)
*G09B 25/02* (2006.01)
(Continued)

(52) U.S. Cl.
CPC ................. *G01N 33/24* (2013.01); *B01J 3/03* (2013.01); *C10L 3/108* (2013.01); *E21B 43/01* (2013.01);
(Continued)

(58) Field of Classification Search
CPC ......... G01N 33/24; E21B 43/01; E21B 49/00; E21B 43/16; E21B 41/0099; B01J 3/03;
(Continued)

(56) References Cited

U.S. PATENT DOCUMENTS 9,841,531 B2 * 12/2017 Li ........................ G01V 99/005
9,970,267 B2 * 5/2018 Li ........................ E21B 41/0092
(Continued)

FOREIGN PATENT DOCUMENTS

CN 102678090 9/2012
CN 103257079 8/2013
(Continued)

OTHER PUBLICATIONS

"International Search Report (Form PCT/ISA/210) of PCT/CN2019/076791," dated Jun. 6, 2019, with English translation thereof, pp. 1-4.

*Primary Examiner* — Ryan D Walsh
(74) *Attorney, Agent, or Firm* — JCIP Global Inc.

(57) ABSTRACT

A pressure-control temperature-control hypergravity experimental device includes a high pressure reactor, a hydraulic oil station, a manifold board, a hypergravity water pressure control module, a hypergravity mining control module, a kettle body temperature control module, and a data collection box. The hydraulic oil station is connected to the
(Continued)

manifold board and then two paths are formed. The two paths are respectively connected to the high pressure reactor via the hypergravity water pressure control module and the hypergravity mining control module. The kettle body temperature control module is connected to the high pressure reactor. The high pressure reactor, the manifold board, the data collection box, the hypergravity water pressure control module and the hypergravity mining control module are disposed on a hypergravity centrifuge air-conditioning chamber. The hydraulic oil station, a computer and the kettle body temperature control module are disposed outside the hypergravity centrifuge air-conditioning chamber.

11 Claims, 3 Drawing Sheets

(51) Int. Cl.

| | | |
|---|---|---|
| *E21B 43/01* | (2006.01) | |
| *B01J 3/03* | (2006.01) | |
| *E21B 49/00* | (2006.01) | |
| *C10L 3/10* | (2006.01) | |
| *E21B 41/00* | (2006.01) | |
| *E21B 43/16* | (2006.01) | |
| *B01J 12/02* | (2006.01) | |

(52) U.S. Cl.
CPC .............. *E21B 49/00* (2013.01); *G09B 25/02* (2013.01); *B01J 12/02* (2013.01); *B01J 2219/00011* (2013.01); *E21B 41/0099* (2020.05); *E21B 43/16* (2013.01)

(58) Field of Classification Search
CPC .. B01J 2219/00011; B01J 12/02; C10L 3/108; G09B 25/02
See application file for complete search history.

(56) References Cited

U.S. PATENT DOCUMENTS

| | | | |
|---|---|---|---|
| 10,408,728 B2 * | 9/2019 | Li | ............................... B01J 3/03 |
| 2015/0337196 A1 | 11/2015 | Kang et al. | |

FOREIGN PATENT DOCUMENTS

| | | | | |
|---|---|---|---|---|
| CN | 203324193 U | * | 12/2013 | |
| CN | 104405345 | | 3/2015 | |
| CN | 104674784 | | 6/2015 | |
| CN | 108386164 A | * | 8/2018 | |
| CN | 108490151 A | * | 9/2018 | |
| CN | 112031714 B | * | 7/2021 | |
| CN | 113072990 A | * | 7/2021 | |

* cited by examiner

PRESSURE-CONTROL TEMPERATURE-CONTROL HYPERGRAVITY EXPERIMENTAL DEVICE FOR SIMULATING DEEP-SEA SEABED RESPONSES

CROSS-REFERENCE TO RELATED APPLICATION

This application is a 371 of international application of PCT application serial no. PCT/CN2019/076791, filed on Mar. 4, 2019, which claims the priority benefit of China application no. 201810178557.2, filed on Mar. 5, 2018 and China application no. 201810178558.7, filed on Mar. 5, 2018. The entirety of each of the above mentioned patent applications is hereby incorporated by reference herein and made a part of this specification.

BACKGROUND

Technical Field

The disclosure relates to a hypergravity physical simulation experimental system in the field of geotechnical engineering, and in particular to a natural gas hydrate depressurization mining hypergravity simulation system/a natural gas hydrate heat shock method mining simulation device under hypergravity conditions.

Description of Related Art

The development of marine energy is one of the key directions to break through the energy bottleneck of the world. In the past 10 years, 60% of the newly discovered oil and gas fields in the world are marine oil and gas fields, and the development of marine oil and gas resources will be the focus in the future. The deep-sea natural gas hydrate reserves are huge, and the calorific value of combustion per unit volume is 10 times that of coal and 2 to 5 times that of traditional natural gas. The deep-sea natural gas hydrate is the preferred alternative energy source for conventional fossil energy in the future. The natural gas hydrate refers to a clathrate crystalline compound formed from natural gas and water under high pressure and low temperature, and mainly exists in the deep-sea high pressure and low temperature environment.

The artificial mining method breaks the phase equilibrium state of natural gas hydrate for natural gas hydrate to decompose and to be then mined to the ground. At present, the depressurization mining method is considered to be one of the most efficient mining methods. The depressurization mining breaks the phase equilibrium state of natural gas hydrate through reducing pressure for natural gas hydrate to decompose, which may become an effective method for large-scale natural gas hydrate mining in the future. The heat shock method is the most widely adopted mining method in laboratory research. The heat shock method heats the natural gas hydrate reservoir through various heating technologies, so that the temperature of the reservoir reaches the decomposition temperature of natural gas hydrate, and breaks the phase equilibrium state, thereby decomposing to produce methane gas. The depressurization-heat injection combined mining method is currently considered to be one of the mining methods with higher mining efficiency and optimal cost control. The reservoir below the deep-sea seabed is the carrier for the occurrence and phase change of natural gas hydrate, evolution, and catastrophe. From bottom to top, the deep-sea seabed is generally composed of a free gas layer, a hydrate layer, and an overlying trap layer. The evolution process thereof determines hydration accumulation, and mining efficiency and safety. Gas and water are produced by phase change decomposition during natural gas hydrate mining. The migration of formed gas and water in the reservoir causes pore pressure, seepage channels, and soil particle pore structure, which affect the effective stress of the soil and seriously affect the physical and mechanical properties of the reservoir, such as permeability, compressibility, shear strength, etc., and even trigger various geological and engineering disasters, such as submarine landslides, hydrate mining wellhead collapse, pipeline fractures, etc., thereby causing significant losses.

The phase change of deep-sea natural gas hydrate mining involves complex interactions of temperature field, seepage field, stress field, and deformation field, and the self-weight stress field directly affects the reservoir change process in the multi-field interaction. At present, the normal gravity (1 g) experimental device is limited by the size of the model, is difficult to simulate the self-weight stress field of a deep reservoir, and cannot realistically reflect the multi-field interaction of the reservoir. The hypergravity (ng) experimental device is equipped with a hypergravity centrifuge, which uses hypergravity to reproduce the real effective stress of the reservoir, so that the stress state of the model is similar to that of the prototype, and the natural gas hydrate mining and engineering catastrophe process in the deep-sea high pressure and low temperature environment of the prototype can be reproduced. At present, the natural gas hydrate simulation mining experimental devices in the world all lack the experimental conditions of the hypergravity environment, and cannot implement the real-scale simulation of geological stress conditions. Therefore, researching a safe, efficient, and economical deep-sea natural gas hydrate mining method based on a hypergravity experimental device is an effective way to alleviate the increasing pressure on energy.

SUMMARY

In order to solve the technical issue of the lack of natural gas hydrate hypergravity mining in the prior art, especially the technical issue of the lack of deep-sea high pressure and low temperature environment simulation under hypergravity conditions in the prior art, the objective of the disclosure is to provide a pressure control temperature control hypergravity experimental device for simulating deep-sea seabed responses, which can study seabed soil catastrophic responses during natural gas hydrate depressurization/heat shock mining in the hypergravity environment, and can realistically simulate the deep-sea high pressure and low temperature environment in the hypergravity environment to carry out experimental research on the multi-mode processes of mining, evolution, and catastrophe during the deep-sea natural gas hydrate reservoir evolution process.

The disclosure comprehensively simulates the mining process and soil layer responses of the deep-sea natural gas hydrate deposition layers in the in-situ stress field by using the depressurization method and the heat shock method. Such function is mainly implemented through simulating depressurization heat shock in the hypergravity environment and the depressurization-heat shock combined mining method to mine natural gas hydrate. The hypergravity environment refers to the ng hypergravity experimental environment that uses the rotation of a hypergravity centrifuge to produce n times the gravitational acceleration g, which can reproduce the large-scale and long-duration processes of marine rock-soil-liquid-gas migration and engineering catastrophe under complex environmental conditions on a model scale.

The disclosure is implemented through the following technical solutions:

1. An Implementation

The disclosure includes a high pressure reactor, a hydraulic oil station, a manifold board, a hypergravity water pressure control module, a hypergravity mining control module, a kettle body temperature control module, and a data collection box. The hydraulic oil station is connected to the manifold board through an oil pipe centrifuge rotary joint, and then two paths are formed. The two paths are respectively connected to the high pressure reactor via the hypergravity water pressure control module and the hypergravity mining control module. The kettle body temperature control module is connected to the high pressure reactor through a water bath passage centrifuge rotary joint. The high pressure reactor, the manifold board, the data collection box, the hypergravity water pressure control module, and the hypergravity mining control module are all disposed on a hypergravity centrifuge in a hypergravity centrifuge air-conditioning chamber. The hydraulic oil station, a computer, and the kettle body temperature control module are disposed outside the hypergravity centrifuge air-conditioning chamber. Sensors in the high pressure reactor, the hypergravity mining control module, the hypergravity water pressure control module, and the kettle body temperature control module are all connected to the data collection box.

The high pressure reactor is a cylindrical stainless steel reactor kettle with a centrifugal acceleration range of 1 to 200 g, a pressure resistance range of 5 to 30 MPa, and an inner cavity volume of 10 to 300 L. The inner cavity of the high pressure reactor serves as a three-dimensional cavity. A natural gas hydrate deposition model and an overlying water layer are disposed in the three-dimensional cavity. A top portion of the high pressure reactor is disposed with a simulated well inlet. A simulated well extends into the three-dimensional cavity through the simulated well inlet and extends to the bottom. The top portion of the high pressure reactor is disposed with a liquid inlet and a safety valve interface. The safety valve interface is communicated with the outside atmosphere via a safety valve. An upper opening of the simulated well is the simulated well inlet.

After the three-dimensional cavity is added to a soil layer, liquid is injected through the liquid inlet and is pressurized to form the overlying water layer. Then, methane gas is injected into the soil layer to form the natural gas hydrate deposition model in the normal gravity environment.

The high pressure reactor is disposed with a temperature measurement interface, a total pressure measurement interface, a pore pressure measurement interface, a piezoelectric ceramic bending element measurement interface, and a time domain reflection measurement interface. The temperature measurement interface, the total pressure measurement interface, the pore pressure measurement interface, the piezoelectric ceramic bending element measurement interface, and the time domain reflection measurement interface may be respectively connected and installed with a pore pressure sensor, a total pressure sensor, a temperature sensor, a piezoelectric ceramic bending element, and a time domain reflection probe. The pore pressure sensor, the total pressure sensor, and the temperature sensor are all installed inside the high pressure reactor. The temperature measurement interface, the total pressure measurement interface, and the pore pressure measurement interface are configured to lead the lead-wires of the pore pressure sensor, the total pressure sensor, and the temperature sensor out of the high pressure reactor to be connected to the data collection box. The piezoelectric ceramic bending element and the time domain reflection probe are both installed on the inner wall of the high pressure reactor. The lead-wires of the piezoelectric ceramic bending element and the time domain reflection probe are led out of the high pressure reactor through the piezoelectric ceramic bending element measurement interface and the time domain reflection measurement interface to be connected to the data collection box.

The pore pressure sensor detects the pressure of pore liquid and gas in the natural gas hydrate deposition model. The total pressure sensor detects the total pressure of three phases of solid, liquid, and gas in the natural gas hydrate deposition model. The temperature sensor detects the temperature in the natural gas hydrate deposition model. The piezoelectric ceramic bending element detects the elastic wave velocity of the natural gas hydrate deposition model. The time domain reflection probe detects the saturation of the natural gas hydrate deposition model.

The overlying water layer of the disclosure is servo-controlled by the hypergravity water pressure control module to a certain stable value between 10 and 20 MPa, so as to simulate the actual water pressure in the deep-sea environment.

The hydraulic oil station and the manifold board are connected through the oil pipe centrifuge rotary joint.

The hypergravity water pressure control module includes a water pressure electrohydraulic servo valve and a water pressure servo booster. One of the paths output by the manifold board is connected to the water pressure servo booster via the water pressure electrohydraulic servo valve. The output end of the water pressure servo booster is connected to the liquid inlet of the high pressure reactor.

The hypergravity mining control module includes an oil pressure electrohydraulic servo valve, a hydraulic servo booster, a servo back pressure valve, a collection pipeline, a liquid storage tank, and a gas storage tank. The other one of the paths output by the manifold board is connected to the hydraulic servo booster via the oil pressure electrohydraulic servo valve. The output end of the hydraulic servo booster is connected to the pressure control end of the servo back pressure valve. The simulated well inlet on top of the high pressure reactor outputs gas and liquid, and is connected to the liquid storage tank via the servo back pressure valve. The liquid storage tank is connected to the gas storage tank. A magnetic float-level gauge is installed on the liquid storage tank. The total pressure sensor is installed on the gas storage tank.

The servo back pressure valve has three openings, including an upper pressure control end, a lower front inlet, and a lower rear outlet. The upper pressure control end is connected to the hydraulic servo booster. The oil pressure at the pressure control end of the servo back pressure valve is controlled through the output oil, thereby controlling the passage connection and disconnection of the servo back pressure valve, so that the collection pipeline and the liquid storage tank are connected or disconnected. The output liquid and gas of the high pressure reactor pass through the collection pipeline to the liquid storage tank or are blocked.

The kettle body temperature control module includes a refrigeration unit, a low temperature water bath box, a refrigeration circulating pump, and a water bath jacket. The water bath jacket is sleeved on the outer wall of the high pressure reactor and is connected to a cold water inlet and outlet. The refrigeration unit is connected to the low temperature water bath box and provides a cold water source. The output end of the low temperature water bath box is connected to a bottom inlet of the water bath jacket via the refrigeration circulating pump. A middle outlet of the water bath jacket is connected to the input end of the low temperature water bath box.

The refrigeration circulating pump and the bottom inlet of the water bath jacket are connected through a water bath passage centrifuge rotary joint, and the middle outlet of the water bath jacket and the input end of the low temperature water bath box are connected through a water bath passage centrifuge rotary joint.

The temperature sensor, the total pressure sensor, the pore pressure sensor, the piezoelectric ceramic bending element, and the time domain reflection probe installed and disposed in the high pressure reactor, the magnetic float-level gauge, the total pressure sensor, and the oil pressure electrohydraulic servo valve in the hypergravity mining control module, and the water pressure electrohydraulic servo valve are all connected to the data collection box. The data collection box is electrically connected to the computer outside the hypergravity centrifuge air-conditioning chamber.

2. Another Implementation

The disclosure includes a high pressure reactor, a hydraulic oil station, a manifold board, a hypergravity water pressure control module, a hypergravity heat shock module, a hypergravity gas-liquid separation module, a kettle body temperature control module, a data collection box, and a computer. The hydraulic oil station is connected to the manifold board through an oil pipe centrifuge rotary joint, and afterwards, two paths are formed. The two paths are respectively connected to the high pressure reactor via the hypergravity water pressure control module and the hypergravity heat shock module. The hypergravity gas-liquid separation module is directly connected to the high pressure reactor. The kettle body temperature control module is connected to the high pressure reactor through a water bath passage centrifuge rotary joint. The high pressure reactor, the manifold board, the data collection box, the hypergravity water pressure control module, the hypergravity heat shock module, and the hypergravity gas-liquid separation module are all disposed on a hypergravity centrifuge in a hypergravity centrifuge air-conditioning chamber. The hydraulic oil station, the computer, and the kettle body temperature control module are disposed outside the hypergravity centrifuge air-conditioning chamber. The high pressure reactor, the hypergravity water pressure control module, the hypergravity heat shock module, the hypergravity gas-liquid separation module, and a sensor in the kettle body temperature control module are all connected to the data collection box.

The high pressure reactor is a cylindrical stainless steel reactor kettle with a centrifugal acceleration range of 1 to 200 g, a pressure resistance range of 5 to 30 MPa, and an inner cavity volume of 10 to 300 L. The inner cavity of the high pressure reactor serves as a three-dimensional cavity. A natural gas hydrate deposition model and an overlying water layer are disposed in the three-dimensional cavity. The top of the high pressure reactor is disposed with a simulated well inlet. A simulated well extends into the three-dimensional cavity through the simulated well inlet and extends to the bottom. The top of the high pressure reactor is disposed with a liquid inlet, a hydrothermal solution inlet, and a safety valve interface. The safety valve interface is communicated with the outside atmosphere via a safety valve. An upper opening of the simulated well is the simulated well inlet.

After the three-dimensional cavity is added to a soil layer, liquid is injected through the liquid inlet and is pressurized to form the overlying water layer. Then, methane gas is injected into the soil layer to form the natural gas hydrate deposition model in the normal gravity environment. The high pressure reactor is disposed with a temperature measurement interface, a total pressure measurement interface, a pore pressure measurement interface, a piezoelectric ceramic bending element measurement interface, and a time domain reflection measurement interface. The temperature measurement interface, the total pressure measurement interface, the pore pressure measurement interface, the piezoelectric ceramic bending element measurement interface, and the time domain reflection measurement interface may be respectively connected and installed with a pore pressure sensor, a total pressure sensor, a temperature sensor, a piezoelectric ceramic bending element, and a time domain reflection probe. The pore pressure sensor, the total pressure sensor, and the temperature sensor are all installed inside the high pressure reactor. The temperature measurement interface, the total pressure measurement interface, and the pore pressure measurement interface are configured to lead the lead-wires of the pore pressure sensor, the total pressure sensor, and the temperature sensor out of the high pressure reactor to be connected to the data collection box. The piezoelectric ceramic bending element and the time domain reflection probe are both installed on the inner wall of the high pressure reactor. The lead-wires of the piezoelectric ceramic bending element and the time domain reflection probe are led out of the high pressure reactor through the piezoelectric ceramic bending element measurement interface and the time domain reflection measurement interface to be connected to the data collection box.

The pore pressure sensor detects the pressure of pore liquid and gas in the natural gas hydrate deposition model. The total pressure sensor detects the total pressure of three phases of solid, liquid, and gas in the natural gas hydrate deposition model. The temperature sensor detects the temperature in the natural gas hydrate deposition model. The piezoelectric ceramic bending element detects the elastic wave velocity of the natural gas hydrate deposition model. The time domain reflection probe detects the saturation of the natural gas hydrate deposition model.

The overlying water layer of the disclosure is servo-controlled by the hypergravity water pressure control module to a certain stable value between 10 and 20 MPa, so as to restore the actual water pressure of the deep-sea environment.

The hydraulic oil station and the manifold board are connected through the oil pipe centrifuge rotary joint.

The hypergravity water pressure control module includes a water pressure electrohydraulic servo valve and a water pressure servo booster. One of the paths output by the manifold board is connected to the water pressure servo booster via the water pressure electrohydraulic servo valve. The output end of the water pressure servo booster is connected to the liquid inlet of the high pressure reactor.

The hypergravity heat shock module sequentially includes a heat injection electrohydraulic servo valve, a working solution servo booster, and an electric heater. The other one of the paths output by the manifold board is connected to the working solution servo booster via the heat injection electrohydraulic servo valve. The output end of the working solution servo booster is connected to the hydrothermal solution inlet of the high pressure reactor via the electric heater.

The hypergravity gas-liquid separation module includes a collection pipeline, an electronically controlled shut-off valve, a liquid storage tank, and a gas storage tank. The electronically controlled shut-off valve is connected to the simulated well inlet on the top of the high pressure reactor. The simulated well inlet on top of the high pressure reactor outputs gas and liquid, and is connected to the liquid storage tank via the electronically controlled shut-off valve. The liquid storage tank is connected to the gas storage tank. A magnetic float-level gauge is installed on the liquid storage tank. The total pressure sensor is installed on the gas storage tank.

The working solution servo booster may add liquid of a specific pressure to the electric heater under hypergravity conditions. The electric heater may heat a working solution to a hydrothermal solution of the required temperature under hypergravity conditions. The electric heater has a lower inlet and an upper outlet. A cooling solution enters from the lower inlet, and the hydrothermal solution exits from the upper outlet. The electronically controlled shut-off valve may control the connection and disconnection of the pipeline through signals under hypergravity conditions.

The kettle body temperature control module includes a refrigeration unit, a low temperature water bath box, a refrigeration circulating pump, and a water bath jacket. The water bath jacket is sleeved on the outer wall of the high pressure reactor and is connected to a cold water inlet and outlet. The refrigeration unit is connected to the low temperature water bath box and provides a cold water source. The output end of the low temperature water bath box is connected to a bottom inlet of the water bath jacket via the refrigeration circulating pump. A middle outlet of the water bath jacket is connected to the input end of the low temperature water bath box.

The refrigeration circulating pump and the bottom inlet of the water bath jacket are connected through a water bath passage centrifuge rotary joint, and the middle outlet of the water bath jacket and the input end of the low temperature water bath box are connected through a water bath passage centrifuge rotary joint.

The temperature sensor, the total pressure sensor, the pore pressure sensor, the piezoelectric ceramic bending element, and the time domain reflection probe installed and disposed in the high pressure reactor, the magnetic float-level gauge and the total pressure sensor in the hypergravity gas-liquid separation module, the heat injection electrohydraulic servo valve and the electric heater in the hypergravity heat shock module, the water pressure electrohydraulic servo valve, and the electronically controlled shut-off valve are all connected to the data collection box. The data collection box is electrically connected to the computer outside the hypergravity centrifuge air-conditioning chamber.

The hypergravity heat shock module, the hypergravity gas-liquid separation module, and the computer are all disposed on the hypergravity centrifuge in the hypergravity centrifuge air-conditioning chamber. The hypergravity heat shock module and the hypergravity gas-liquid separation module are both connected to the sensor in the kettle body temperature control module, which are all connected to the data collection box.

The booster may adopt the form of a plunger pump structure, that is, the water pressure servo booster may adopt a control water pressure servo plunger pump, and the hydraulic servo booster may adopt a hydraulic servo plunger pump.

Under the above two implementations of the disclosure, the high pressure reactor works in the hypergravity environment. The pressure of the overlying water layer is controlled through the hypergravity water pressure control module. The temperature environment around the natural gas hydrate is controlled through the kettle body temperature control module. The decompression decomposition and production measurement of the natural gas hydrate are performed through the hypergravity mining control module to simulate on-site mining. Alternatively, the heat shock method of the natural gas hydrate is performed through the hypergravity heat shock module to simulate on-site mining, and the production measurement is performed through the hypergravity gas-liquid separation module.

Under the above two implementations of the disclosure, the experimental device may operate in the hypergravity centrifuge, simulate the pressure of the overlying water layer and the self-weight stress of the deep-sea natural gas hydrate deposition layer, and reproduce the real deep-sea natural gas hydrate deposition layer. A vertical well depressurization method is performed on the deep-sea natural gas hydrate deposition layer for the mining experiment. Alternatively, a vertical heat shock method is performed on the deep-sea natural gas hydrate deposition layer for the mining experiment by disposing a vertical well and a heat injection opening. The sensor is used to test the changes in model temperature, pore pressure, total pressure, elastic wave velocity, saturation, and other parameters due to natural gas hydrate mining. Soil layer responses and catastrophic process of on-site natural gas hydrate mining are realistically simulated, which provides scientific support for natural gas hydrate mining simulation experiment.

In summary, the beneficial effects of the disclosure are as follows.

1) This experimental device can simulate soil layer stress field through the hypergravity centrifuge, simulate deep-sea pore water pressure through the hypergravity water pressure control module, and simulate the deep-sea temperature environment through the kettle body temperature control module. Compared with the existing normal gravity experimental device, the biggest advantage is that this experimental device can realistically reproduce the in-situ natural gas hydrate soil layer, explore the catastrophe mechanism of the seabed during deep-sea hydrate mining, and explore the multi-mode processes of mining, evolution, and catastrophe during the deep-sea natural gas hydrate reservoir evolution process to provide effective guidance for natural gas hydrate mining of deep-sea energy.

2) The high pressure reactor, the hypergravity water pressure control module, and the hypergravity mining control module in this experimental device can all work in the hypergravity environment and withstand greater hypergravity centrifugal acceleration.

3) The hydraulic servo booster and the servo back pressure valve in the hypergravity mining control module may effectively, quickly, and accurately control the well inlet pressure in the hypergravity environment, and simulate the real natural gas hydrate mining process using the depressurization method. Alternatively, the working solution servo booster and the electric heater in the hypergravity heat shock module may effectively and quickly supply the required temperature to the hydrothermal solution or hot steam, and simulate the real natural gas hydrate mining process using the heat shock method.

4) According to the hypergravity scaling effect, the simulated well extended into the three-dimensional cavity in this experimental device may reproduce the well-soil interaction mechanism of the real mining process.

5) The biggest advantage of the experimental device of the disclosure compared with the existing normal gravity experimental device is that this experimental device restores the actual seabed stress field through the hypergravity field, thereby exploring the catastrophe mechanism of the seabed during deep-sea hydrate mining and the multi-mode processes of mining, evolution, and catastrophe during the deep-sea natural gas hydrate reservoir evolution process to provide references for natural gas hydrate mining.

DETAILED DESCRIPTION OF DISCLOSED EMBODIMENTS

The content of the disclosure will be further described below with reference to the drawings and embodiments.

Embodiment 1

Figure 1:
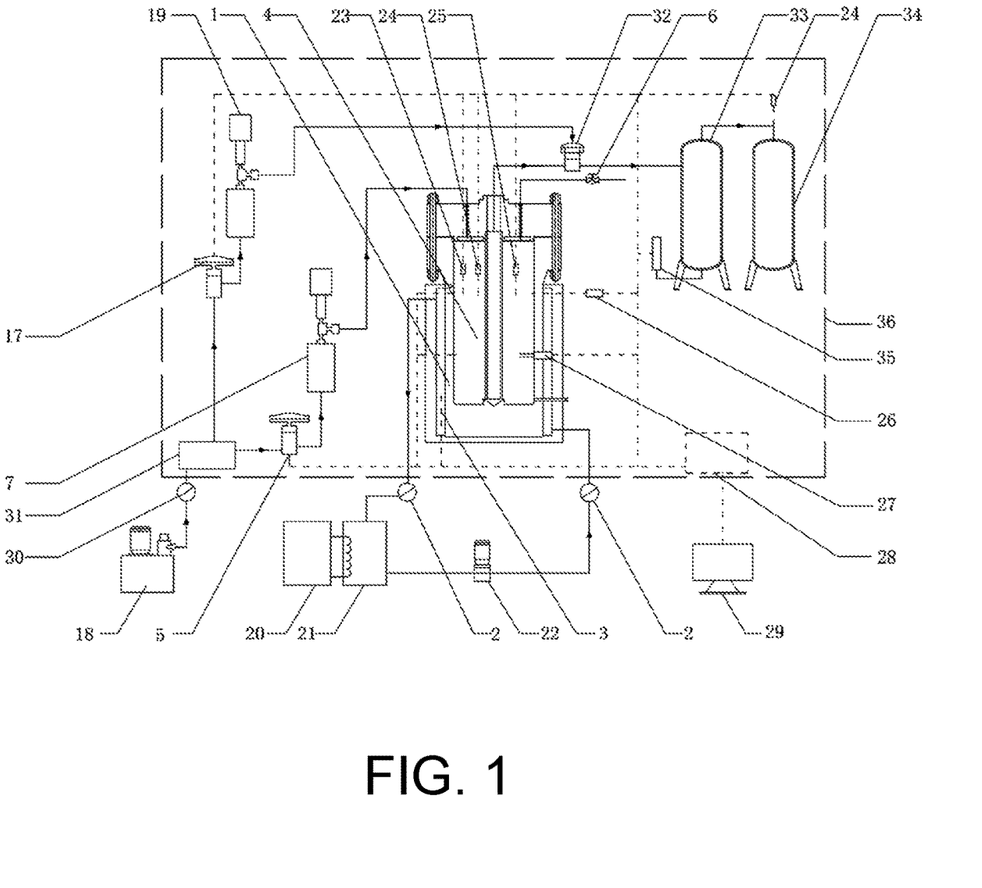
FIG. 1 is a schematic diagram of a structure according to Embodiment 1 of the disclosure.

As shown in FIG. 1, the specific implementation of the disclosure includes a high pressure reactor 1, a hydraulic oil station 18, a manifold board 31, a hypergravity water pressure control module, a hypergravity mining control module, a kettle body temperature control module, a data collection box 28, and a computer 29. The hydraulic oil station 18 is connected to the manifold board 31 through the oil pipe centrifuge rotary joint 30, and afterwards, the two paths are formed. The two paths are respectively connected to the high pressure reactor 1 via the hypergravity water pressure control module and the hypergravity mining control module. The kettle body temperature control module is connected to the high pressure reactor 1 through a water bath passage centrifuge rotary joint 2. The high pressure reactor 1, the manifold board 31, the data collection box 28, the hypergravity water pressure control module, and the hypergravity mining control module are disposed on a hypergravity centrifuge in a hypergravity centrifuge air-conditioning chamber 36. The hydraulic oil station 18, the computer 29, and the kettle body temperature control module are disposed outside the hypergravity centrifuge air-conditioning chamber 36. Sensors in the high pressure reactor 1, the hypergravity mining control module, the hypergravity water pressure control module, and the kettle body temperature control module are all connected to the data collection box 28.

The high pressure reactor 1 is a cylindrical high pressure resistant stainless steel reactor kettle working with a centrifugal acceleration range of 50 to 200 g, a pressure resistance range of 5 to 30 MPa, and an inner cavity volume of 10 to 300 L. The pressure resistance range is preferably 20±2 MPa, the three-dimensional cavity volume is preferably 280±20 L, and the height of the three-dimensional cavity is greater than 500 mm.

The inner cavity of the high pressure reactor 1 serves as a three-dimensional cavity 4. A natural gas hydrate deposition model and an overlying water layer are disposed in the three-dimensional cavity 4. A top portion of the high pressure reactor 1 is disposed with a simulated well. The simulated well extends into the three-dimensional cavity 4 through a simulated well inlet and extends to a bottom of the three-dimensional cavity 4. The top portion of the high pressure reactor 1 is disposed with a liquid inlet and a safety valve interface. The safety valve interface is communicated with the outside atmosphere via a safety valve 6. After the three-dimensional cavity 4 is added to a soil layer, liquid is injected through the liquid inlet and is pressurized to form the overlying water layer. Then, methane gas is injected into the soil layer to form the natural gas hydrate deposition model in the normal gravity environment.

In the high pressure reactor 1, 1 pair of piezoelectric ceramic bending element measurement interfaces, 1 time domain reflection measurement interface, 3 total pressure measurement interfaces, 3 pore pressure measurement interfaces, and 3 temperature measurement interfaces are disposed. The piezoelectric ceramic bending element measurement interfaces, the time domain reflection measurement interface, the total pressure measurement interfaces, the pore pressure measurement interfaces, and the temperature measurement interfaces are respectively connected and installed with a pore pressure sensor 23, a total pressure sensor 24, a temperature sensor 25, a piezoelectric ceramic bending element 26, and a time domain reflection probe 27. The pore pressure sensor 23, the total pressure sensor 24, and the temperature sensor 25 are all installed inside the high pressure reactor 1. The piezoelectric ceramic bending element 26 and the time domain reflection probe 27 are both installed on the inner wall of the high pressure reactor 1. The pore pressure sensor 23, the total pressure sensor 24, the temperature sensor 25, the piezoelectric ceramic bending element 26, and the time domain reflection probe 27 respectively measure the pore pressure, total pressure, temperature, elastic wave velocity, saturation, and other parameters of the natural gas hydrate deposition model in the three-dimensional cavity 4, and the measured data is imported into the computer 29 through the data collection box 28 for analysis and processing. In the specific implementation, the number of the above-mentioned devices or equipment may also be increased or decreased according to the requirements or scale of the experiment.

The data collection box 28 collects the pressure in a gas storage tank 34, the output water volume in a magnetic float-level gauge 35, the feedback signals of the water pressure electrohydraulic servo valve 5 and the oil pressure electrohydraulic servo valve 17, and the signals of the pore pressure sensor 23, the total pressure sensor 24, the temperature sensor 25, the piezoelectric ceramic bending element 26, and the time domain reflection probe 27 in the three-dimensional cavity 4. The data collection box 28 may perform online measurement and monitoring of saturation, elastic wave velocity, total pressure, pore pressure, temperature, and other parameters in the hypergravity environment and display the instantaneous values and cumulative values thereof. The data processing of each sensor generally includes a time-total pressure curve, a time-pore pressure curve, a time-saturation curve, a time-elastic wave velocity curve, etc., so as to study soil layer responses due to natural gas hydrate decomposition under real stress field.

In specific implementation, sequentially connected data collection block, data processing block, and data storage block are disposed in the computer 29. The data collection block is connected with the data collection box. The data processing block is a data processing software, which processes the signals of each sensor. The data storage block may store a processing result of the data processing block.

The hypergravity water pressure control module controls the pressure of the overlying water layer on the three-dimensional cavity 4 when the hypergravity centrifuge is working, and includes the water pressure electrohydraulic servo valve 5 and a water pressure servo booster 7. One of the paths output by the manifold board 31 is connected to the water pressure servo booster 7 via the water pressure electrohydraulic servo valve 5. The output end of the water pressure servo booster 7 is connected to a liquid inlet of the high pressure reactor 1. The water pressure electrohydraulic servo valve 5 outputs an oil pressure signal to the water pressure servo booster 7. The water pressure servo booster 7 has its own water storage tank, converts the oil pressure signal into a water pressure signal, and directly outputs water pressure to control the pressure of the overlying water layer. The water pressure electrohydraulic servo valve 5 and the water pressure servo booster 7 can both work at a centrifugal acceleration of 1 to 200 g. The water pressure servo booster 7 may servo-control the output pressure of the booster through the pressure signal at the output end and the water pressure electrohydraulic servo valve 5, thereby achieving the function of stable pressure control.

Figure 3:
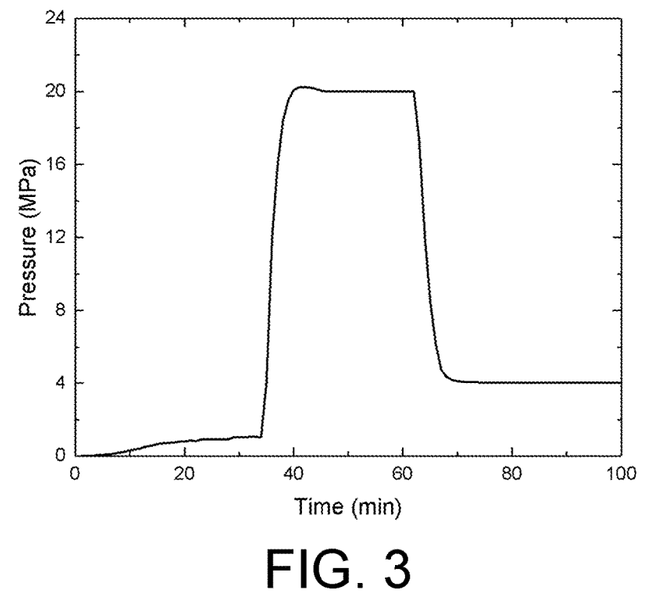
FIG. 3 is a pressure control performance graph of a servo plunger pump under hypergravity according to an embodiment of the disclosure.

In the specific implementation, the boosters all adopt a plunger pump structure. FIG. 3 shows the internal fluid pressure control performance curve of the servo plunger pump in a 100 g hypergravity environment individually controlling the high pressure reactor 1. A plunger pump is used to simulate the control from an internal pressure of 1 MPa before hydrate formation to an internal pressure of 20 MPa when hydrate is formed. Then, a stable pressure of 20 MPa during the hydrate formation process is simulated. Finally, pressure reduction is servo-controlled during hydrate mining. The actual measurement results show that the servo plunger pump 7 may achieve the function of remotely servo-controlling pressure.

The hypergravity mining control module is mainly used to control the pressure of a simulated well outlet in the high pressure reactor 1 in the hypergravity environment and output measurement, and includes an oil pressure electrohydraulic servo valve 17, a hydraulic servo booster 19, a servo back pressure valve 32, a collection pipeline, a liquid storage tank 33, and a gas storage tank 34. The other one of the paths output by the manifold board 31 is connected to the hydraulic servo booster 19 via the oil pressure electrohydraulic servo valve 17. The output end of the hydraulic servo booster 19 is connected to the pressure control end of the servo back pressure valve 32. The simulated well inlet of the high pressure reactor 1 is connected to the liquid storage tank 33 via the servo back pressure valve 32. The liquid storage tank 33 is connected to the gas storage tank 34. A magnetic float-level gauge 35 is installed on the liquid storage tank 33. The total pressure sensor 24 is installed on the gas storage tank 34. The oil pressure electrohydraulic servo valve 17 and the hydraulic servo booster 19 cooperate to output oil pressure. The output end of the hydraulic servo booster 19 is connected to the upper pressure control end of the servo back pressure valve 32, thereby controlling the passage connection and disconnection of the servo back pressure valve 32 to control the outlet pressure. The simulated well inlet on the top portion of the high pressure reactor 1 outputs gas and liquid, and is connected to a lower front inlet of the servo back pressure valve 32 via the collection pipeline. A lower rear outlet of the servo back pressure valve 32 is connected to the liquid storage tank 33. Under the action of centrifugal force, the liquid storage tank 33 also has the function of a gas-liquid separator, which can separate the produced gas and liquid while measuring the liquid production. The amount of produced gas is data converted through the total pressure sensor in the gas storage tank 34.

Figure 4:
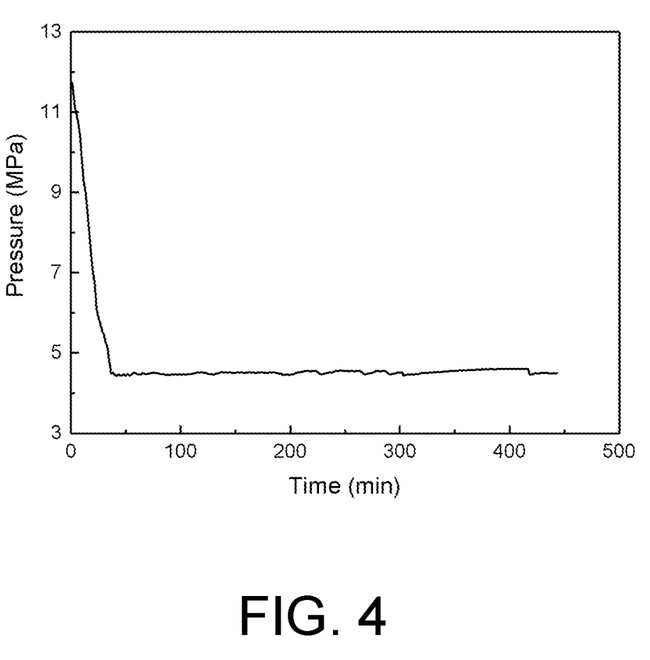
FIG. 4 is a pressure-time graph of a depressurization experiment in a hypergravity environment according to Embodiment 1 of the disclosure.

FIG. 4 shows the mining well pressure actual measurement-time curve during the depressurization mining simulation experiment in a 100 g hypergravity environment using the module. The module simulates the reduction and stabilization of the internal pressure of the high pressure reactor from 12 MPa to 4 MPa during the hydrate mining process. The actual measurement results show that the pressure reduction during the hydrate simulation mining experiment may be servo-controlled through the module, and the mining experiment may be stably performed.

The kettle body temperature control module is configured to control the temperature of the high pressure reactor 1 through circulating cold water, and includes a refrigeration unit 20, a low temperature water bath box 21, a refrigeration circulating pump 22, and a water bath jacket 3. The water bath jacket 3 is sleeved on the outer wall of the high pressure reactor 1 and is connected to a cold water inlet and outlet. The refrigeration unit 20 is connected to the low temperature water bath box 21 and provides a cold water source. The output end of the low temperature water bath box 21 is connected to a bottom inlet of the water bath jacket 3 via the refrigeration circulating pump 22. A middle outlet of the water bath jacket 3 is connected to the input end of the low temperature water bath box 21. The refrigeration circulating pump 22 and the bottom inlet of the water bath jacket 3, and the middle outlet of the water bath jacket 3 and the input end of the low temperature water bath box 21 are both connected through a water bath passage centrifuge rotary joint 2.

The specific working process of the disclosure is as follows.

The high pressure reactor 1 prepared with the natural gas hydrate deposition model is disposed on a hypergravity centrifuge basket. The relevant pipelines of the hypergravity water pressure control module, the hypergravity mining control module, and the kettle body temperature control module are connected to the high pressure reactor 1. The cold water circulation of the kettle body temperature control module is turned on to stabilize the temperature of the high pressure reactor kettle. The water pressure servo booster 7 of the hypergravity water pressure control module is turned on to stably control the pressure of the overlying water layer of the three-dimensional cavity 4. All lead-wires of the sensors are connected to the data collection box 28.

After setting, the hypergravity centrifuge is turned on, and the centrifugal acceleration is gradually increased from 1 g to 200 g. During the acceleration process, the device needs to control the cold water circulation of the kettle wall through the kettle body temperature control module, and maintain the stable pressure of the overlying water layer through the hypergravity water pressure control module. The remaining sensors monitor model responses during the acceleration process, and output data to the data collection box 28.

After reaching the required centrifugal acceleration for the experiment, the natural gas hydrate depressurization mining hypergravity experiment begins. After ensuring that the temperature of the kettle body and the pressure of the overlying water layer are stable, the hypergravity mining control module is turned on. The upper pressure control end of the servo back pressure valve 32 is controlled through the hydraulic servo booster 19 to gradually decrease to the required pressure value. Due to the balance of forces, the lower front inlet of the servo back pressure valve 32 gradually opens, and the pressure of the simulated well of the high pressure reactor 1 begins to decrease. The pressure reduction process is implemented through the combination of the hydraulic servo booster 19 and the servo back pressure valve 32, and the range is 5 MPa to 20 MPa. After the pressure of the simulated well is reduced, the natural gas hydrate in the three-dimensional cavity 4 is decomposed. The produced water and gas are pumped out of the high pressure reactor 1 due to the pressure difference, and reach the liquid storage tank 33 after passing through the servo back pressure valve 32. The centrifugal force field is used to implement the separation of the produced gas and liquid the liquid storage tank 33, and the gas is transported to the gas storage tank 34 via the pipeline. The sensor monitors model responses during the experiment and outputs data to the data collection box 28.

After the experiment, the device is shut down. The centrifugal acceleration is gradually reduced to 1 g. After the pressure in the high pressure reactor 1 is released to normal pressure, the kettle is opened for cleaning. The experiment ends.

Embodiment 2

Figure 2:
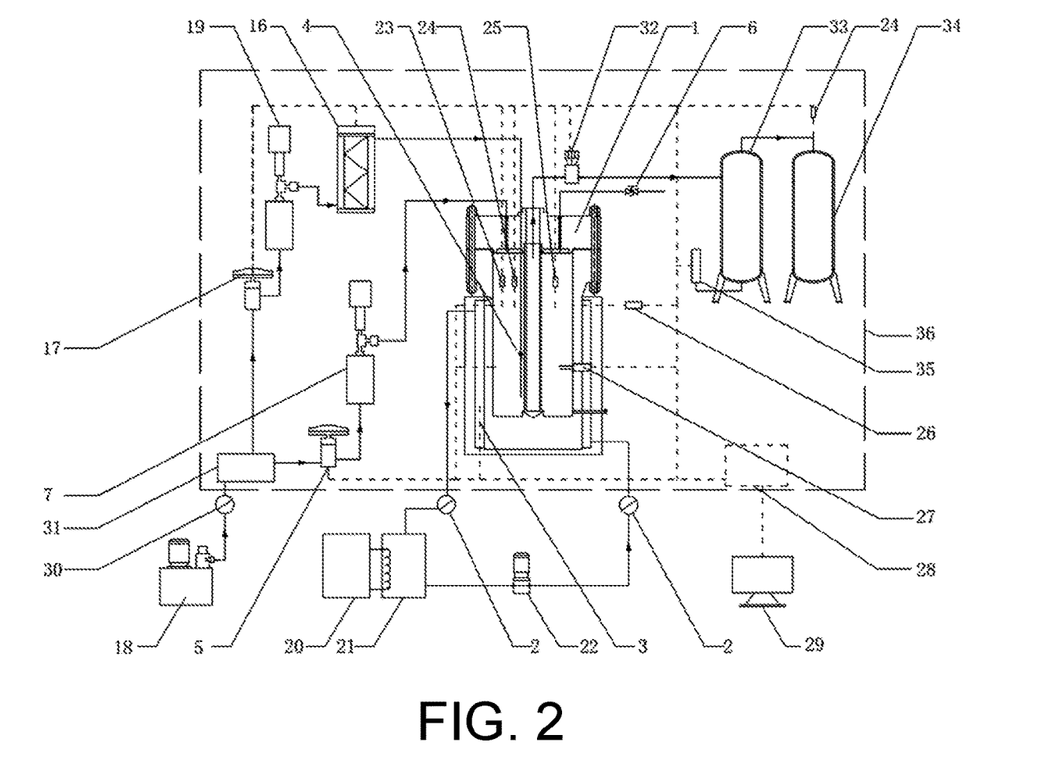
FIG. 2 is a schematic diagram of a structure according to Embodiment 2 of the disclosure.

As shown in FIG. 2, the specific implementation of the disclosure includes a high pressure reactor 1, a hydraulic oil station 18, a manifold board 31, a hypergravity water pressure control module, a hypergravity heat shock module, a hypergravity gas-liquid separation module, a kettle body temperature control module, a data collection box 28, and a computer 29. The hydraulic oil station 18 is connected to the manifold board 31 through an oil pipe centrifuge rotary joint 30, and afterwards, two paths are formed. The two paths are respectively connected to the high pressure reactor 1 via the hypergravity water pressure control module and the hypergravity heat shock module. The hypergravity gas-liquid separation module is directly connected to the high pressure reactor 1. The kettle body temperature control module is connected with the high pressure reactor 1 through a water bath passage centrifuge rotary joint 2. The high pressure reactor 1, the manifold board 31, the data collection box 28, the hypergravity water pressure control module, the hypergravity heat shock module, and the hypergravity gas-liquid separation module are disposed on a hypergravity centrifuge in a hypergravity centrifuge air-conditioning chamber 36. The hydraulic oil station 18, the computer 29, and the kettle body temperature control module are disposed outside the hypergravity centrifuge air-conditioning chamber 36. The high pressure reactor 1, the hypergravity heat shock module, the hypergravity water pressure control module, the hypergravity gas-liquid separation module, and a sensor in the kettle body temperature control module are all connected to the data collection box 28.

The high pressure reactor 1 is a cylindrical high pressure resistant stainless steel reactor kettle working with a centrifugal acceleration range of 50 to 200 g, a pressure resistance range of 5 to 30 MPa, and an inner cavity volume of 10 to 300 L. The pressure resistance range is preferably 20±2 MPa, the three-dimensional cavity volume is preferably 280±20 L, and the height of the three-dimensional cavity is greater than 500 mm.

The inner cavity of the high pressure reactor 1 serves as a three-dimensional cavity 4. A natural gas hydrate deposition model and an overlying water layer are disposed in the three-dimensional cavity 4. The top portion of the high pressure reactor 1 is disposed with a simulated well. The simulated well extends into the three-dimensional cavity 4 through a simulated well inlet and extends to the bottom of the three-dimensional cavity 4. The top portion of the high pressure reactor 1 is disposed with a liquid inlet, a hydrothermal solution inlet, and a safety valve interface. The safety valve interface is communicated with the outside atmosphere via a safety valve 6. After the three-dimensional cavity 4 is added to a soil layer, liquid is injected through the liquid inlet and is pressurized to form the overlying water layer. Then, methane gas is injected into the soil layer to form the natural gas hydrate deposition model in the normal gravity environment.

In the high pressure reactor 1, 1 pair of piezoelectric ceramic bending element measurement interfaces, 1 time domain reflection measurement interface, 3 total pressure measurement interfaces, 3 pore pressure measurement interfaces, and 3 temperature measurement interfaces are disposed. The piezoelectric ceramic bending element measurement interfaces, the time domain reflection measurement interface, the total pressure measurement interfaces, the pore pressure measurement interfaces, and the temperature measurement interfaces are respectively connected and installed with a pore pressure sensor 23, a total pressure sensor 24, a temperature sensor 25, a piezoelectric ceramic bending element 26, and a time domain reflection probe 27. The pore pressure sensor 23, the total pressure sensor 24, and the temperature sensor 25 are all installed inside the high pressure reactor 1. The piezoelectric ceramic bending element 26 and the time domain reflection probe 27 are both installed on the inner wall of the high pressure reactor 1. The pore pressure sensor 23, the total pressure sensor 24, the temperature sensor 25, the piezoelectric ceramic bending element 26, and the time domain reflection probe 27 respectively measure the pore pressure, total pressure, temperature, elastic wave velocity, saturation, and other parameters of the natural gas hydrate deposition model in the three-dimensional cavity 4, and the measured data is imported into the computer 29 through the data collection box 28 for analysis and processing. In the specific implementation, the number of the above-mentioned devices or equipment may also be increased or decreased according to the requirements or scale of the experiment.

The data collection box 28 collects the pressure in a gas storage tank 34, the output water volume in a magnetic float-level gauge 35, the feedback signals of the water pressure electrohydraulic servo valve 5 and a heat injection electrohydraulic servo valve 17, and the signals of the pore pressure sensor 23, the total pressure sensor 24, the temperature sensor 25, the piezoelectric ceramic bending element 26, and the time domain reflection probe 27 in the three-dimensional cavity 4. The data collection box 28 may perform online measurement and monitoring of saturation, elastic wave velocity, total pressure, pore pressure, temperature, and other parameters in the hypergravity environment and display the instantaneous values and cumulative values thereof. The data processing of each sensor generally includes a time-total pressure curve, a time-pore pressure curve, a time-saturation curve, a time-elastic wave velocity curve, etc., so as to study soil layer responses due to natural gas hydrate decomposition under real stress field.

In specific implementation, sequentially connected data collection block, data processing block, and data storage block are disposed in the computer 29. The data collection block is connected with the data collection box. The data processing block is a data processing software, which processes the signals of each sensor. The data storage block may store a processing result of the data processing block.

The hypergravity water pressure control module controls the pressure of the overlying water layer on the three-dimensional cavity 4 when the hypergravity centrifuge is working, and includes the water pressure electrohydraulic servo valve 5 and a water pressure servo booster 7. One of the paths output by the manifold board 31 is connected to the water pressure servo booster 7 via the water pressure electrohydraulic servo valve 5. The output end of the water pressure servo booster 7 is connected to a liquid inlet of the high pressure reactor 1. The water pressure electrohydraulic servo valve 5 outputs an oil pressure signal to the water pressure servo booster 7. The water pressure servo booster 7 has its own water storage tank, converts the oil pressure signal into a water pressure signal, and directly outputs water pressure to control the pressure of the overlying water layer. The water pressure electrohydraulic servo valve 5 and the water pressure servo booster 7 can both work at a centrifugal acceleration of 1 to 200 g. The water pressure servo booster 7 may servo-control the output pressure of the booster through the pressure signal at the output end and the water pressure electrohydraulic servo valve 5, thereby achieving the function of stable pressure control.

The hypergravity heat shock module mainly injects hydrothermal solution or steam into the high pressure reactor 1 in the hypergravity environment, and includes the heat injection electrohydraulic servo valve 17, a working solution servo booster 19, and an electric heater 16. The other one of the paths output by the manifold board 31 is connected to the working solution servo booster 19 via the heat injection electrohydraulic servo valve 17. The output end of the working solution servo booster 19 is connected to a lower inlet of the electric heater 16, and an upper outlet of the electric heater 16 outputs the hydrothermal solution. The heat injection electrohydraulic servo valve 17 outputs an oil pressure signal to the working solution servo booster 19. The working solution servo booster 19 provides a working solution at a specific pressure, which is heated in the electric heater and is injected into the three-dimensional cavity 4 via a hydrothermal solution inlet on the top portion of the high pressure reactor 1.

The hypergravity gas-liquid separation module mainly separates and collects the gas and liquid output from the high pressure reactor 1 under hypergravity conditions, and measures the output, and includes a collection pipeline, an electronically controlled shut-off valve 32, a liquid storage tank 33, and a gas storage tank 34. The simulated well inlet of the high pressure reactor 1 is connected to the liquid storage tank 33 via the electronically controlled shut-off valve 32. A magnetic float-level gauge 35 is installed on the liquid storage tank 33. The total pressure sensor 24 is installed on the gas storage tank 34. The computer 29 provides signals through the data collection box 28 to control the passage connection and disconnection of the electronically controlled shut-off valve 32. Under the action of centrifugal force, the liquid storage tank 33 also has the function of a gas-liquid separator, which can separate the produced gas and liquid while measuring the liquid production. The amount of produced gas is data converted through the total pressure sensor in the gas storage tank 34.

The kettle body temperature control module is configured to control the temperature of the high pressure reactor 1 through circulating cold water, and includes a refrigeration unit 20, a low temperature water bath box 21, a refrigeration circulating pump 22, and a water bath jacket 3. The water bath jacket 3 is sleeved on the outer wall of the high pressure reactor 1 and is connected to a cold water inlet and outlet. The refrigeration unit 20 is connected to the low temperature water bath box 21 and provides a cold water source. The output end of the low temperature water bath box 21 is connected to a bottom inlet of the water bath jacket 3 via the refrigeration circulating pump 22. A middle outlet of the water bath jacket 3 is connected to the input end of the low temperature water bath box 21. The refrigeration circulating pump 22 and the bottom inlet of the water bath jacket 3, and the middle outlet of the water bath jacket 3 and the input end of the low temperature water bath box 21 are both connected through a water bath passage centrifuge rotary joint 2.

The specific working process of the disclosure is as follows.

The high pressure reactor 1 prepared with the natural gas hydrate deposition model is disposed on a hypergravity centrifuge basket. The relevant pipelines of the hypergravity water pressure control module, the hypergravity heat shock module, the hypergravity gas-liquid separation module, and the kettle body temperature control module are connected to the high pressure reactor 1. The cold water circulation of the kettle body temperature control module is turned on to stabilize the temperature of the high pressure reactor kettle. The water pressure servo booster 7 of the hypergravity water pressure control module is turned on to stably control the pressure of the overlying water layer of the three-dimensional cavity 4. All lead-wires of the sensors are connected to the data collection box 28.

After setting, the hypergravity centrifuge is turned on, and the centrifugal acceleration is gradually increased from 1 g to 200 g. During the acceleration process, the device needs to control the cold water circulation of the kettle wall through the kettle body temperature control module, and maintain the stable pressure of the overlying water layer through the hypergravity water pressure control module. The remaining sensors monitor model responses during the acceleration process, and output data to the data collection box 28.

After reaching the required centrifugal acceleration for the experiment, the natural gas hydrate heat shock hypergravity experiment begins. After ensuring that the temperature controlled by the kettle body temperature control module and the pressure of the overlying water layer controlled by the hypergravity water pressure control module are stable, the hypergravity heat shock module is turned on. The working solution servo booster 19 provides a working solution at a specific pressure to the electric heater 16, which is quickly heated to 40 to 60° C. by the electric heater 16, and a hydrothermal solution at a specific pressure is output. After the hydrothermal solution is injected into the three-dimensional cavity 4 via a hydrothermal solution inlet on the top portion of the high pressure reactor 1, the hydrothermal solution inlet is closed. After soaking for a period of time, the natural gas hydrate is fully thermally decomposed. The computer 29 is used to control the electronically controlled shut-off valve 32 to open. The gas and water produced by the decomposition of the natural gas hydrate in the three-dimensional cavity 4 are output to the high pressure reactor 1 and reach the liquid storage tank 33. The centrifugal force field is used to separate the produced gas and liquid in the liquid storage tank 33, and the gas is transported to the gas storage tank 34 via the pipeline. The sensors monitor model responses during the experiment, and output data to the data collection box 28.

After the experiment, the device is shut down. The centrifugal acceleration is gradually reduced to 1 g. After the pressure in the high pressure reactor 1 is released to normal pressure, the kettle is opened for cleaning. The experiment ends.

This specification only exemplifies the preferred embodiments of the disclosure, and all equivalent technical exchanges made under the working principles and ideas of the disclosure are regarded as within the protection scope of the disclosure.

What is claimed is:

1. A pressure-controlled temperature-controlled hypergravity experimental device for simulating deep-sea seabed responses, comprising: a high pressure reactor, a hydraulic oil station, a manifold board, a hypergravity water pressure control module, a hypergravity mining control module, a kettle body temperature control module, and a data collection box, wherein the hydraulic oil station is connected to the manifold board and then two paths are formed, the two paths are respectively connected to the high pressure reactor via the hypergravity water pressure control module and the hypergravity mining control module; the kettle body temperature control module is connected to the high pressure reactor; the high pressure reactor, the data collection box, the hypergravity water pressure control module, and the hypergravity mining control module are all disposed on a hypergravity centrifuge in a hypergravity centrifuge air-conditioning chamber, the hydraulic oil station and the kettle body temperature control module are disposed outside the hypergravity centrifuge air-conditioning chamber, and sensors in the high pressure reactor, the hypergravity mining control module, the hypergravity water pressure control module and the kettle body temperature control module are all connected to the data collection box.

2. The pressure-controlled temperature-controlled hypergravity experimental device for simulating deep-sea seabed responses according to claim 1, wherein after a three-dimensional cavity is added to a soil layer, liquid is injected through a liquid inlet and is pressurized to form an overlying water layer, and methane gas is then injected into the soil layer to form a natural gas hydrate deposition model in a normal gravity environment.

3. The pressure-controlled temperature-controlled hypergravity experimental device for simulating deep-sea seabed responses according to claim 1, wherein the high pressure reactor is disposed with a temperature measurement interface, a total pressure measurement interface, a pore pressure measurement interface, a piezoelectric ceramic bending element measurement interface, and a time domain reflection measurement interface; the temperature measurement interface, the total pressure measurement interface, the pore pressure measurement interface, the piezoelectric ceramic bending element measurement interface, and the time domain reflection measurement interface are able to be respectively connected and installed with a pore pressure sensor, a total pressure sensor, a temperature sensor, a piezoelectric ceramic bending element, and a time domain reflection probe; the pore pressure sensor, the total pressure sensor, and the temperature sensor are all installed inside the high pressure reactor, the temperature measurement interface, the total pressure measurement interface, and the pore pressure measurement interface are configured to lead lead-wires of the pore pressure sensor, the total pressure sensor and the temperature sensor out of the high pressure reactor, and the lead-wires are connected to the data collection box; the piezoelectric ceramic bending element and the time domain reflection probe are both installed on an inner wall of the high pressure reactor, lead-wires of the piezoelectric ceramic bending element and the time domain reflection probe are led out of the high pressure reactor through the piezoelectric ceramic bending element measurement interface and the time domain reflection measurement interface, and are connected to the data collection box.

4. The pressure-controlled temperature-controlled hypergravity experimental device for simulating deep-sea seabed responses according to claim 1, wherein the hydraulic oil station and the manifold board are connected through an oil pipe centrifuge rotary joint.

5. The pressure-controlled temperature-controlled hypergravity experimental device for simulating deep-sea seabed responses according to claim 1, wherein the hypergravity water pressure control module comprises a water pressure electrohydraulic servo valve and a water pressure servo booster; one of the paths output by the manifold board is connected to the water pressure servo booster via the water pressure electrohydraulic servo valve, and an output end of the water pressure servo booster is connected to a liquid inlet of the high pressure reactor.

6. The pressure-controlled temperature-controlled hypergravity experimental device for simulating deep-sea seabed responses according to claim 1, wherein the kettle body temperature control module comprises a refrigeration unit, a low temperature water bath box, a refrigeration circulating pump, and a water bath jacket; the water bath jacket is sleeved on an outer wall of the high pressure reactor and is connected to a cold water inlet and outlet, the refrigeration unit is connected to the low temperature water bath box and provides a cold water source, an output end of the low temperature water bath box is connected to a bottom inlet of the water bath jacket via the refrigeration circulating pump, and a middle outlet of the water bath jacket is connected to an input end of the low temperature water bath box.

7. The pressure-controlled temperature-controlled hypergravity experimental device for simulating deep-sea seabed responses according to claim 6, wherein the refrigeration circulating pump and the bottom inlet of the water bath jacket are connected through a water bath passage centrifuge rotary joint, and the middle outlet of the water bath jacket and the input end of the low temperature water bath box are connected through a water bath passage centrifuge rotary joint.

8. The pressure-controlled temperature-controlled hypergravity experimental device for simulating deep-sea seabed responses according to claim 1, wherein the hypergravity mining control module comprises an oil pressure electrohydraulic servo valve, a hydraulic servo booster, a servo back pressure valve, a collection pipeline, a liquid storage tank, and a gas storage tank; another one of the paths output by the manifold board is connected to the hydraulic servo booster via the oil pressure electrohydraulic servo valve, an output end of the hydraulic servo booster is connected to a pressure control end of the servo back pressure valve; a simulated well inlet on a top portion of the high pressure reactor outputs gas and liquid, and is connected to the liquid storage tank via the servo back pressure valve, and the liquid storage tank is connected to the gas storage tank; a magnetic float-level gauge is installed on the liquid storage tank, and a total pressure sensor is installed on the gas storage tank; and the high pressure reactor is a cylindrical stainless steel reactor kettle, an inner cavity of the high pressure reactor serves as a three-dimensional cavity, and a natural gas hydrate deposition model and an overlying water layer are disposed in the three-dimensional cavity; the top portion of the high pressure reactor is disposed with the simulated well inlet, a simulated well extends into the three-dimensional cavity through the simulated well inlet and extends to a bottom of the three-dimensional cavity; the top portion of the high pressure reactor is disposed with a liquid inlet and a safety valve interface, the safety valve interface is communicated with outside atmosphere via a safety valve, and an upper opening of the simulated well is the simulated well inlet.

9. The pressure-controlled temperature-controlled hypergravity experimental device for simulating deep-sea seabed responses according to claim 8, wherein a temperature sensor, a total pressure sensor, a pore pressure sensor, a piezoelectric ceramic bending element and a time domain reflection probe installed and disposed in the high pressure reactor, the magnetic float-level gauge, the total pressure sensor and the oil pressure electrohydraulic servo valve in the hypergravity mining control module, and a water pressure electrohydraulic servo valve are all connected to the data collection box, and the data collection box is electrically connected to a computer outside the hypergravity centrifuge air-conditioning chamber.

10. The pressure-controlled temperature-controlled hypergravity experimental device for simulating deep-sea seabed responses according to claim 1, wherein the hypergravity mining control module includes a hypergravity heat shock module and a hypergravity gas-liquid separation module, the device further comprising a computer, and the hypergravity gas-liquid separation module is directly connected to the high pressure reactor; the hypergravity heat shock module sequentially comprises a heat injection electrohydraulic servo valve, a working solution servo booster and an electric heater; another one of the paths output by the manifold board is connected to the working solution servo booster via the heat injection electrohydraulic servo valve, and an output end of the working solution servo booster is connected to a hydrothermal solution inlet of the high pressure reactor via the electric heater; the hypergravity gas-liquid separation module comprises a collection pipeline, an electronically controlled shut-off valve, a liquid storage tank and a gas storage tank; the electronically controlled shut-off valve is connected to a simulated well inlet on a top portion of the high pressure reactor; the simulated well inlet on the top portion of the high pressure reactor outputs gas and liquid, and is connected to the liquid storage tank via the electronically controlled shut-off valve, and the liquid storage tank is connected to the gas storage tank; a magnetic float-level gauge is installed on the liquid storage tank, and a total pressure sensor is installed on the gas storage tank; and the high pressure reactor is a cylindrical stainless steel reactor kettle; an inner cavity of the high pressure reactor serves as a three-dimensional cavity, and a natural gas hydrate deposition model and an overlying water layer are disposed in the three-dimensional cavity; the top portion of the high pressure reactor is disposed with the simulated well inlet, a simulated well extends into the three-dimensional cavity through the simulated well inlet and extends to a bottom of the three-dimensional cavity; the top portion of the high pressure reactor is disposed with a liquid inlet, a hydrothermal solution inlet and a safety valve interface, the safety valve interface is communicated with outside atmosphere via a safety valve, and an upper opening of the simulated well is the simulated well inlet.

11. The pressure-controlled temperature-controlled hypergravity experimental device for simulating deep-sea seabed responses according to claim 10, wherein a temperature sensor, a total pressure sensor, a pore pressure sensor, a piezoelectric ceramic bending element and a time domain reflection probe installed and disposed in the high pressure reactor, the magnetic float-level gauge and the total pressure sensor in the hypergravity gas-liquid separation module, the heat injection electrohydraulic servo valve and the electric heater in the hypergravity heat shock module, a water pressure electrohydraulic servo valve and the electronically controlled shut-off valve are all connected to the data collection box, and the data collection box is electrically connected to a computer outside the hypergravity centrifuge air-conditioning chamber.

\* \* \* \* \*